United States Patent
Msika et al.

(10) Patent No.: US 7,863,472 B2
(45) Date of Patent: Jan. 4, 2011

(54) PROCESS FOR PRODUCING REFINED AVOCADO OIL RICH IN TRIGLYCERIDES, AND OIL OBTAINABLE BY SAID PROCESS

(75) Inventors: Philippe Msika, Versailles (FR); Jacques Legrand, Neuilly sur Eure (FR)

(73) Assignee: Laboratories Expanscience, Courbevoie (FR)

( * ) Notice: Subject to any disclaimer, the term of this patent is extended or adjusted under 35 U.S.C. 154(b) by 0 days.

(21) Appl. No.: 12/395,425

(22) Filed: Feb. 27, 2009

(65) Prior Publication Data

US 2009/0163590 A1 Jun. 25, 2009

Related U.S. Application Data

(62) Division of application No. 11/600,178, filed on Nov. 16, 2006.

(60) Provisional application No. 60/737,745, filed on Nov. 18, 2005.

(30) Foreign Application Priority Data

Nov. 18, 2005 (FR) .................................. 05 11702

(51) Int. Cl.
 *C07C 57/00* (2006.01)
(52) U.S. Cl. ........................... 554/227; 554/224; 554/9; 554/15; 554/16; 514/547
(58) Field of Classification Search ............... 554/9, 554/15, 16, 224, 227; 514/547
See application file for complete search history.

(56) References Cited

U.S. PATENT DOCUMENTS

| 5,262,163 | A | 11/1993 | Rancurel et al. |
| 5,334,290 | A | 8/1994 | Nuns et al. |
| 5,650,157 | A | 7/1997 | Bockow |
| 6,994,875 | B2 | 2/2006 | Piccirilli et al. |
| 7,029,713 | B2 | 4/2006 | Msika et al. |
| 2003/0108650 | A1 | 6/2003 | Kohler et al. |
| 2004/0081703 | A1 | 4/2004 | Dupont et al. |

FOREIGN PATENT DOCUMENTS

| EP | 0 493 144 B1 | 7/1992 |
| EP | 1 250 144 B1 | 10/2002 |
| ER | 1250 144 B1 | 10/2002 |
| FR | 2 653 974 A1 | 5/1991 |
| FR | 2 678 632 A1 | 11/1993 |
| FR | 2 792 202 B1 | 10/2000 |
| FR | 2 803 752 A1 | 7/2001 |
| FR | 2 806 260 A1 | 9/2001 |
| GB | 1 191 180 A | 5/1970 |
| WO | WO-2006/004388 A1 | 12/2006 |

OTHER PUBLICATIONS

Southwell et al: "Extraction and refining of oil obtained from dried avocado fruit using a small expeller", XP009066801, Jul. 3, 1989, Trop. Sci. vol. 30, pp. 121-131.
Moreno et al: "Effect of different extraction methods on fatty acids, volatile compounds, and physical and chemical properties of avocado oil". XP002381544, J. Agric. Food chem. 2003, vol. 51, pp. 2216-2221.
Werman et al: "The effect of avocado oils on some liver characteristics in growing rats", vol. 27, No. 5, pp. 279-282, 1989, Food Chem. Toxic.
Salazar M J et al.; Effect of an avocado oil-rich diet over an angiotensin II-induced blood pressure response:, Journal of Ethnopharmacology, Elsevier Scientific Publishers Ltd, vol. 98, No. 3, Apr. 26, 2005, XP004824076.
Layne KS et al., "Normal subjects consuming physiological levels of 18:3(n-3) and 20:5(n-3) from flaxseed or fish oils have characteristics differences in plasma lipid and lipoprotien fatty acid levels", J. Nutr., vol. 126, 1996, pp. 2130-2140, XP002526738.

*Primary Examiner*—Deborah D Carr
(74) *Attorney, Agent, or Firm*—Birch, Stewart, Kolasch & Birch, LLP

(57) ABSTRACT

The present invention concerns a process for producing refined avocado oil rich in triglycerides. The invention also pertains to refined avocado oil rich in triglycerides obtainable by said process. Advantageously, the refined avocado oil of the invention contains a sterols-enriched unsaponifiable fraction. Advantageously, the refined avocado oil of the invention is substantially free of acetogenins and furanic lipids. The invention also concerns compositions containing said oil. The invention also pertains to such compositions for use as a medication, as a dermatological agent, as a cosmetic agent, or as a nutriceutical, for human or animal use.

16 Claims, No Drawings

PROCESS FOR PRODUCING REFINED AVOCADO OIL RICH IN TRIGLYCERIDES, AND OIL OBTAINABLE BY SAID PROCESS

CROSS-REFERENCE TO RELATED APPLICATIONS

The present application is a 37 C.F.R. §1.53(b) divisional of U.S. application Ser. No. 11/600,178 filed Nov. 16, 2006, which in turn claims priority on French Application No. 0511702 filed Nov. 18, 2005 and U.S. Provisional Application No. 60/737,745 filed Nov. 18, 2005. The entire contents of each of these applications is hereby incorporated by reference.

The present invention relates to a process for producing refined avocado oil which is rich in triglycerides. The invention also relates to refined avocado oil rich in triglycerides obtainable by said process. Advantageously, the refined avocado oil of the invention contains an unsaponifiable fraction which is concentrated in sterols. Advantageously, the refined avocado oil of the invention is substantially free of acetogenins and furanic lipids. The invention also relates to compositions containing said oil. The invention also relates to such compositions for use as a medication, as a dermatological agent, as a cosmetic agent, or as a nutriceutical, for human or animal use.

Avocados, which originate from Mexico, were brought to Europe by the Spanish Conquistadors. The fruit has become a very popular food. Avocados are rich in oil, since the lipids represent between 10% and 20% of the fresh fruit. The high fat content is one of the characteristics of the fruit. The oil, which has a fatty acid profile which very closely resembles that of olive oil, has been used for many years in cosmetic and pharmaceutical applications. Further, because of its nutritional properties, its importance as a food grade oil or food supplement has grown in recent years, and global production is constantly increasing.

Unrefined or virgin avocado oil is generally extracted by a process known as cold pressing, which consists of mixing and macerating fresh fruit in water followed by separating three phases: solid, oily and aqueous, in a centrifugal decanter. A final phase of polishing by centrifugal clarification produces perfectly clear oil. Other processes such as cold pressing with the addition of solid adjuvants, or supercritical extraction, can produce virgin avocado oil.

Refined avocado oil may be obtained from virgin avocado oil or unrefined avocado oil using conventional refining processes such as those generally carried out to produce conventional salad oil, for example sunflower oil, soya oil, or rapeseed oil. Said refining comprises is the following operations:
- demucilagination (mucilage removal);
- neutralization;
- decolorizing;
- winterizing;
- deodorization.

Avocado oil can also be obtained from dried avocados. Heat treating avocados can reduce the residual moisture in the fruit to below 10%, rendering extraction of the oil possible using an organic solvent or mechanical pressure.

However, such extraction processes, which include heating the avocado and solvent extraction or mechanical pressure extraction, modify the composition of the extracted oil. When heating avocado, chemical reactions release compounds which are partially transformed and extracted with the oil. Said compounds are unstable and are not completely eliminated by conventional refining processes. The instability of such compounds renders their elimination difficult during refining without running the risk of transformation into problematical molecules.

Further, such processes cannot be used to prepare refined avocado oils guaranteeing complete harmlessness for food or nutriceutical use. Studies have shown that the unrefined oil obtained from dried avocados including the stone contained compounds which may be toxic: M. J. Werman, S. Mokady, I. Néeman, L. Auslaender, A. Zeidler, Food and Chem. Toxicol 1989, 27, 279. A number of specific constituents of the avocado such as acetogenins, which are toxic compounds, which have been detected in avocado fruits and leaves, have been discovered in avocado oil extracted and refined using prior art processes.

Hence, when conventional refining processes including demucilagination, neutralizing, decolorizing, winterizing and deodorization are carried out, the various treatments are not sufficiently effective to guarantee that unstable compounds are completely eliminated or that they do not degrade into secondary derivatives.

The low stability of certain constituents of the avocado and the risks related to their potential toxicity mean that the fate of said constituents during the various steps of the process to produce a food quality oil must be known. As a result, there exists a need to develop a novel process which can obtain refined avocado oil that does not have the disadvantages of the prior art and that allows completely safe oil from dried avocados to be sold.

The present invention satisfies this need. The Applicant has thus discovered a novel process for producing refined avocado oil, which is very simple to implement, comprising a combination of various operations which can accurately control and monitor the evolution and transformation of various specific constituents of the avocado. The process of the present invention can substantially remove the specific impurities of avocado and guarantee that it is harmless. Hence, drying fruit before extracting oil, and carrying out a step of fractioning the oil, advantageously by molecular distillation, can substantially free substances of avocados which are potentially toxic, such as acetogenins, also known as "persin", and degradation products with a furanic structure that are responsible for bitterness, in particular furanic lipids.

Advantageously, in the present invention, the molecular distillation step, which is judiciously interposed between drying the fruit and refining the oil, can eliminate undesirable and unstable compounds. The process of the invention, including a molecular distillation step upstream of the refining step, results in the preparation of a fraction which is enriched in triglycerides and substantially free of any compound that runs the risk of toxicity or that may result in the formation of derivatives responsible for bitterness in the refined oil.

Further, the process of the present invention can produce high yields of a refined avocado oil rich in triglycerides, containing an unsaponifiable fraction which is enriched in sterols. The oil obtained by said process, or obtainable by said process, may thus advantageously be incorporated into cosmetic, dermatological, or pharmaceutical compositions, or into food compositions, food supplements, or nutriceuticals, for human or animal use. The oil of the present invention also has the advantage of being perfectly clean and clear and thus may readily be incorporated into various types of compositions.

Furthermore, the refined avocado oil obtained using the process of the invention or obtainable by said process is rich in mono-unsaturated fatty acids which are particularly advantageous because they are known to reduce LDL cholesterol in the blood. The oil of the invention is thus particularly suitable for reducing cardiovascular health problems. The refined avocado oil of the invention, which is rich in triglycerides, guarantees it better stability because of its low mono-and diglyceride content.

The present invention thus provides a process for producing refined avocado oil rich in triglycerides, characterized in that it comprises the following steps:

1) dehydrating fresh avocados or avocados which have undergone prior transformations, in controlled manner, advantageously carried out at a temperature in the range −50° C. to 120° C., in particular in the range −50° C. to 90° C.;
2) extracting oil from the dehydrated fruit;
3) fractioning the oil into its fraction rich in triglycerides; then
4) refining the oil fraction rich in triglycerides.

The refined avocado oil advantageously contains an unsaponifiable fraction which is rich in sterols.

The term "refined avocado oil rich in triglycerides" as used in the present invention means a refined avocado oil containing at least 80% by weight of triglycerides, advantageously at least 90% by weight of triglycerides, more advantageously 95% to 99% by weight of triglycerides relative to the total weight of the refined avocado oil.

Particularly advantageously in the present invention, the refined avocado oil contains no more than 1% by weight of monoglycerides, preferably no more than 0.1% by weight of monoglycerides relative to the total weight of the refined avocado oil. Advantageously, the amount of diglycerides present in the oil of the present invention is in the range 1% to 5% by weight, preferably in the range 1.5% to 3% by weight.

The term "avocado which has undergone prior transformations" means the co-products derived from processes for extracting fresh avocado oil, in particular those derived from centrifuging processes. Examples of "avocado which has undergone prior transformations" which may be mentioned are i) avocado milk obtained by pressing pulp, or ii) products from flushing partially de-oiled pulp by centrifuging, by-products generally present at the outlet from centrifuge sieves, or the residues from centrifuges produced during separation.

Other sources of avocado which fall within the scope of the term "avocado which has undergone prior transformations" may also be mentioned: avocado press cake, co-produced during cold pressing of the fruit (fresh or dried) or liquid-solid extraction of avocado oil from fresh or dried fruit using an organic solvent, or the by-products of preparing avocado-based food of the guacamole type, may also constitute an alternative starting material for use in the context of the present invention.

Advantageously, in the present invention, prior to the dehydrating step 1), the freshly harvested avocado fruits undergo a grading step to eliminate fruit which is too ripe, damaged, or is marked. The avocados used are then sliced and are preferably divided into layers which are as regular and as thin as possible, to facilitate rapid, homogeneous drying and/or dehydration.

More generally, the dehydration carried out in step 1) of the process means the techniques known to the skilled person for extracting water from a compound. Techniques which may be mentioned are drying in a stream of hot air or a controlled atmosphere (for example nitrogen), atmospheric pressure or vacuum drying, thin or thick layer drying, as well as microwave drying, spray drying, freeze drying, or osmotic dehydration in solution (for example direct osmosis) or in the solid phase (for example drying in osmotic bags).

In a particular implementation of the present invention, the dehydration step 1) consists in drying the sliced fruit, preferably in a hot air drier at a temperature in the range 70° C. to 90° C., in particular in the range 75° C. to 80° C. The drying period is advantageously in the range 8 hours (h) to 36 h, preferably until a residual level of moisture in the fruit is 5% or less at the outlet from the drier.

In the context of the present process, to facilitate industrial application and for cost reasons, drying in ventilated driers, in a thin layer and in a stream of hot air at a temperature in the range 70° C. to 80° C. for 8 h to 36 h is preferred.

When the dehydration step 1) is carried out by drying at a temperature above ambient temperature, said heat treatment of the avocado, carried out under well-defined conditions, can encourage the molecular transformation of specific compounds of the avocado and can optimize the transformation yield, while avoiding the synthesis of degradation products due to heat or oxidation.

The extraction step 2) may be carried out using any means known to the skilled person, preferably by simple cold pressing or using a solvent at low temperature. Mechanical pressing of the dehydrated fruit can guarantee the quality of the oil and its unsaponifiable constituents, and can result in a high degree of recovery of the oil without using an organic substance such as a solvent.

In a particular implementation of the present invention, the sheets of dehydrated avocados, preferably dehydrated by drying, are ground using a mechanical grinder. The powder obtained is then supplied via a pre-digester to a continuous screw mechanical press. The oil produced by mechanical pressure is decanted then filtered through a filter press.

The fractioning step 3) may be carried out using any means known to the skilled person, and advantageously consists in cold crystallization, vacuum distillation, or molecular distillation. Said fractioning step can separate a fraction that is rich in unsaponifiables from a heavy fraction that is rich in triglycerides. Typically, the unsaponifiable-rich fraction represents 8% to 15% by weight of the unrefined oil and the fraction rich in triglycerides represents 85% to 92% by weight of the unrefined oil.

The unsaponifiable fraction is the fraction of a fat which, after prolonged action of an alkaline base, remains insoluble in water and may be extracted with an organic solvent. Five major groups of substances are present in the majority of unsaponifiables from vegetable oils: saturated or unsaturated hydrocarbons, aliphatic or terpenic alcohols, sterols, tocopherols, and carotenoid and xanthophyllic pigments.

The unsaponifiable-rich fraction generally contains 30% to 80% by weight of unsaponifiables. The fraction rich in triglycerides generally contains at least 80% by weight, advantageously at least 90% by weight, in particular 95% to 99% by weight of triglycerides. The fraction rich in triglycerides itself also contains unsaponifiables, in general 0.5% to 1.5% by weight relative to the total weight of the fraction rich in triglycerides. These unsaponifiables are concentrated into sterols.

The fractioning step 3), advantageously carried out by molecular distillation, can substantially remove specific compounds of the avocado, such as potentially toxic acetogenins and their transformation or degradation compounds, in particular furanic lipids responsible for bitterness.

Said step 3) can also isolate, without thermal degradation, the concentrated fraction of unsaponifiables and the concentrated fraction of triglycerides. Further, it can greatly reduce the fatty acid content of the fraction rich in triglycerides, facilitating the subsequent refining step such as neutralization, and limiting product loss.

An additional advantage of the fractioning step 3), preferably carried out by molecular distillation, consists in its ability to fractionate constituents of the unsaponifiable compounds. During the distillation step, sterols, present in the form of fatty acid esters, in contrast to non esterified sterols and to all of the other constituents of the unsaponifiables, do not have a low enough boiling point for distillation. The esterified sterol compounds are thus concentrated in the portion of unsaponifiables contained in the heavy fraction of the avocado oil which is rich in triglycerides. Sterols in the form of sterol esters thus form the majority of the compounds in the unsaponifiables following the oil fractioning step.

In accordance with a particular feature of the present invention, the fractioning step 3) is carried out by molecular distillation, allowing practically integral separation of the compounds in the unsaponifiable fraction, de-acidification of the triglyceride fraction, and enrichment of the unsaponifiables portion of the triglyceride fraction in sterol esters.

Advantageously, in accordance with the present invention, the unrefined oil from the extraction step 2) is pumped to a continuous degasser prior to the fractioning step 3). The continuous degasser is a falling film apparatus which, prior to distillation, can eliminate any traces of water and dissolved gas.

In accordance with a particular feature of the present invention, the fractioning step 3) is molecular distillation, which may be carried out at a temperature in the range 180° C. to 260° C., advantageously in the range 200° C. to 250° C., more advantageously in the range 220° C. to 230° C., maintaining the pressure in the range $10^{-3}$ mmHg (millimeters of mercury) to $10^{-1}$ mmHg, advantageously in the range $10^{-3}$ mmHg to $10^{-2}$ mmHg.

This molecular distillation step is preferably carried out using a device selected from centrifuge type molecular distillers and wiped film type molecular distillers.

Centrifuge type molecular distillers are known to the skilled person. As an example, European patent application EP-A-0 493 144 describes a molecular distiller of that type. In general, a thin layer of the substance to be distilled is distributed on the heated surface (hot surface) of a conical rotor which rotates at high speed. The distillation chamber is placed under vacuum. Under those conditions, the constituents of the oil such as the unsaponifiables evaporate from rather than boil off the hot surface, the advantage being that the oil and its constituents, in particular the unsaponifiables (which are known to be fragile) are not degraded during evaporation.

Wiped film type molecular distillers, also known to the skilled person, comprise a distillation chamber provided with a rotating wiper, which allows substance for distilling to be distributed continuously on the evaporation surface (hot surface). The product vapors are condensed by a cold finger placed in the center of the distillation chamber. The peripheral supply and vacuum systems are very close to those of a centrifugal distiller (supply pumps, slide vane rotary vacuum pumps, and oil diffusion pumps, etc). The residues and distillates are recovered in glass flasks by gravitational flow.

At the end of the fractioning step 3), the distilled fraction that is rich in unsaponifiables generally represents 5% to 15% by weight of the starting oil, and the distilled fraction that is rich in triglycerides generally represents 85% to 95% by weight of the starting oil.

The fraction rich in triglycerides is then purified by refining.

The refining step 4) advantageously comprises at least one of the following operations: acid treatment, chemical neutralization, decolorization, winterizing, and deodorization. Said refining step can purify the heavy glyceride fraction to obtain a refined avocado oil containing an unsaponifiable fraction that is rich in sterols, which can be used for cosmetic, pharmaceutical, food, or nutriceutical applications, for human or animal use.

Particularly advantageously, the refining step 4) comprises the following set of operations: acid treatment, chemical neutralization, decolorization, winterizing, and deodorization.

Acid treatment is preferably acid conditioning, allowing demucilagination and elimination of phospholipids. The acid treatment is typically carried out using a weak acid, such as phosphoric acid or citric acid, or using a strong acid such as sulfuric acid or hydrochloric acid. Generally, the acid treatment is carried out with stirring, at a temperature in the range 30° C. to 70° C., typically about 50° C. to 60° C.

Other processes may be preferred, such as microfiltration, which is a low-pressure membrane process used to filter colloids, or processes using biotechnology, such as enzymatic demucilagination.

Chemical neutralization, which typically follows the acid treatment, can eliminate free fatty acids, to free the oil of phospholipids which have undergone the conditioning operation, to eliminate trace metals, and to facilitate decolorization by destroying some pigments and colored compounds of oxidative origin. Chemical neutralization is typically carried out using a basic agent such as sodium hydroxide, potassium carbonate, or a tertiary amine (DMHA). The fatty acids are separated, by centrifuging or filtering, in the form of soaps which also contain mucilages and various impurities eliminated during said treatment.

Advantageously, in the present invention, washing is carried out following the chemical neutralization operation, preferably with water. Preferably, the reaction medium is then dried, generally under vacuum at high temperature, for example at 90° C.

Decolorization, which typically follows chemical neutralization, can in general eliminate the colored pigments which neutralization has only very partially destroyed. Decolorization is typically carried out using decolorizing earths and/or charcoal, advantageously until the avocado oil has a clear or very clear color.

The decolorizing earths used are typically natural clays of the montmorillonite type, principally constituted by calcium and magnesium aluminosilicates, activated by acid treatment. The activated charcoal used may be obtained from peat, wood, lignite, coal, or coconut husks. Said products are typically activated at high temperature, either using steam or a chemical process.

The winterizing step, which typically follows decolorization, may be carried out at a temperature in the range 5° C. to 18° C., advantageously for 1 day (d) to 15 d. Typically, the refined avocado oil is steadily cooled, preferably with gentle stirring, to a temperature of the order of 10° C. to 12° C. Generally, the oil is then maintained at this temperature for 48 h, then is filtered under pressure. Winterizing can precipitate triglycerides which are rich in saturated fatty acids. This step is particularly advantageous since it can produce a clean and clear refined avocado oil which does not go cloudy at low temperature, thus guaranteeing a homogeneous appearance regardless of storage conditions.

Deodorization, which typically follows winterizing, can in general eliminate and extract volatile compounds and malodorous molecules. Decolorization is typically carried out at a temperature in the range 150° C. to 210° C., advantageously under vacuum, generally in a stream of saturated steam or nitrogen. Decolorization may, for example, be carried out at a pressure in the range 2 mmHg to 20 mmHg. In particular, decolorizing may be carried out at a temperature of the order of 180° C. to 200° C., at a pressure of the order of 4 mmHg to 6 mmHg. The percentage of vapor injected generally represents 0.5% to 4% of the treated oil. The injection time may be in the range 2 h to 6 h. After drying and cooling, the refined avocado oil is then advantageously packaged under inert gas, away from light and moisture.

The present invention also provides a refined avocado oil that is rich in triglycerides, which may be obtained by the process of the present invention. Advantageously, said oil contains an unsaponifiable fraction that is rich in sterols.

In accordance with a particular characteristic of the present invention, said unsaponifiable fraction contains at least 40% by weight of sterols, advantageously between 45% and 70% by weight of sterols, relative to the total weight of unsaponifiables.

Particularly advantageously, the oil of the present invention is substantially free of acetogenins (persin) or furanic lipids.

The term "substantially free of acetogenins or furanic lipids" as used in the context of the present invention means an oil which does not contain a quantifiable amount of acetogenins or furanic lipids.

Advantageously, said fraction does not contain a quantifiable amount of persin or furanic lipids. Obtaining an oil that is substantially free of acetogenins is particularly advantageous, since acetogenins are potentially toxic, thermally unstable compounds. Under the effect of heat, said compounds result in the formation of furanic lipids which are responsible for bitterness in the oil.

In a particular implementation, the refined avocado oil rich in triglycerides of the present invention contains at most 300 parts per million (ppm) of acetogenins and/or at most 2000 ppm of furanic lipids.

Advantageously, the refined avocado oil rich in triglycerides of the present invention contains at most 100 ppm of acetogenins and at most 500 ppm of furanic lipids relative to the total weight of the oil.

As is known, the avocado includes particular lipids of the aliphatic acetogenin type, the principal component of which is a linoleic acetogenin with formula:

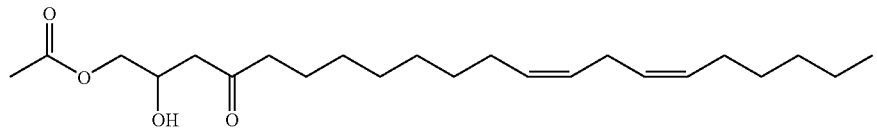

Said compounds are also commonly known under the generic name of persin. Thus, the term "aliphatic acetogenins", as used in the invention, means components with the following formula:

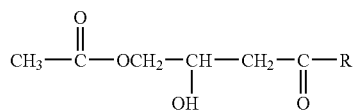

in which R is a linear $C_{11}$-$C_{19}$ hydrocarbon, preferably $C_{13}$-$C_{17}$, which is saturated or comprises one or more ethylenically or acetylenically unsaturated bonds.

The term "furanic lipids of avocado" as used in the present invention means components with the following formula:

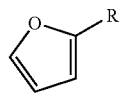

in which R is a linear $C_{11}$-$C_{19}$ hydrocarbon, preferably $C_{13}$-$C_{17}$, which is saturated or comprises one or more ethylenically or acetylenically unsaturated bonds.

Advantageously, the unsaponifiable fraction of the oil of the invention is rich in sterols and the oil may thus be used to reduce cholesterol levels in the blood.

This oil also has a high mono-unsaturated fatty acid content. Oleic acid represents close to ⅔ of the fatty acids of the avocado. Thus, the oil of the invention is advantageously used in preventing cardiovascular diseases.

Further, the high triglycerides content of the oil and its low partial (mono and di) glycerides content demonstrates that the oil is very pure and guarantees a low degree of hydrolysis and good stability.

The present invention also provides a composition containing said refined avocado oil rich in triglycerides. Advantageously, said oil is present in a concentration in the range 5% to 95% by weight, advantageously in the range 10% to 40% by weight relative to the total composition weight.

Particularly advantageously, the compositions of the present invention further comprise at least one compound selected from vegetable oils, vegetable oil unsaponifiables, furanic vegetable oil lipids and mixtures thereof.

Particular vegetable oils which may be mentioned are sunflower oil, palm oil, palm-nut oil, coconut oil, grapeseed oil, black mustard oil, poppy-seed oil, shea butter oil, sweet almond oil, soya oil, avocado oil, peanut oil, cottonseed oil, sesame seed oil, olive oil, corn oil, cacao oil, castor oil, Ben oil, linseed oil, rapeseed oil, annatto oil, wheatgerm oil, safflower oil, lupin oil, walnut oil, hazelnut oil and colza oil. Vegetable oils, the unsaponifiable fraction of which is rich in tocopherols and/or phytosterols, are particularly preferred. This is the case, for example, with soya, corn, rapeseed, or sunflower seed oil.

Advantageously, the compositions contain a refined avocado oil rich in triglycerides of the present invention in combination with avocado oil from fresh fruit.

The compositions of the present invention may also include oils of animal origin or purified compounds rich in omega-3 (eicosapentanoic acid, docohexanoic acid, alpha-linolenic acid, etc), such as fish oil or linseed oil.

The compositions of the present invention may also include omega-6 compounds such as gamma-linolenic acid. In this regard, the compositions of the present invention may contain borage oil, cassis oil, or onager oil (for example 200 mg/d (milligrams/day) to 500 mg/d).

The compositions of the present invention may also include at least one compound selected from: perna calaliculus, yucca, boswellia, amino acids, synthetic and plant peptides, animal and vegetable proteins, bromelain, and yeasts.

The compositions of the present invention may also include natural or synthesized PPAR agonists. Said natural or synthesized PPAR agonists are advantageously selected from: natural ligands, in particular leucotrienes, 8S-HETE, phytanic acid, unsaturated and saturated fatty acids, prostaglandin, (15d-PGJ2), 9-HODE, 13-HODE; synthesized ligands, in particular all of the compounds in the fibrate family (for example fenofibrate), tibrates, anti-inflammatories such as indomethacin, flufenamic acid, ibuprofen and fenoprofen, and glitazones including thiazolidinediones (troglitazone, rosiglitazone, pioglitazone and darglitazone), and mixtures thereof.

Vegetable oil unsaponifiables which may be incorporated into the compositions of the invention are preferably selected from the group constituted by avocado oil unsaponifiables, soya oil unsaponifiables, and mixtures thereof.

An example in accordance with the present invention which may be mentioned is a composition containing about 17% by weight of refined avocado oil rich in triglycerides of the present invention, about 33% by weight of soya oil unsaponifiables and about 50% by weight of a commercially available refined soya oil. This composition may also contain excipients. This composition is advantageously in the form of a 300 mg (milligram) to 5 g (gram) capsule.

Particularly advantageously, the composition of the present invention contains refined avocado oil rich in triglycerides of the present invention and unsaponifiables such as soya oil. As an example, the composition contains about 33% by weight of the refined avocado oil rich in triglycerides of the present invention, and about 67% by weight of soya oil unsaponifiables, optionally with excipients. This composition is advantageously in the form of a 300 mg to 5 g capsule.

The compositions of the invention are advantageously used in the form of a palatable tablet for animals or in the form of a food quality gel for horses.

The constituents of the vegetable oil unsaponifiables in the concentrated or purified form may be incorporated into the compositions of the invention and are preferably selected from the group constituted by phytosterols and phytosterol esters, tocopherols and tocopherol esters, tocotrienols and tocotrienol esters, squalene, avocado fraction I (avocado 1,2,4-trihydroxyaliphatic alcohols), triterpenic alcohols and triterpenic alcohol esters, stanols and stanol esters, aliphatic alcohols and aliphatic alcohol esters, and mixtures thereof.

The compositions of the present invention may also include compounds such as Docteur Théo's product Avosoy, containing a mixture of fatty acids, unsaponifiables (squalene, tocopherols, sterols), and sterols.

The compositions of the present invention may also include compounds such as the Avoflex product from Cyvex, containing a mixture of fatty acids, unsaponifiables (squalene, tocopherols, sterols), and sterols.

The compositions of the present invention may also include compounds such as the Vegeflex and Prevention products from Windmill, containing a mixture of fatty acids, unsaponifiables, tocopherols and sterols, advantageously in combination with glucosamine.

The compositions of the present invention may also include compounds such as the Avosol product from A/S Anjo, containing unsaponifiables in particular.

In a particular implementation of the present invention, the compositions also include at least one compound selected from: amino sugars such as glucosamine; glucosamine salts such as glucosamine hydrochloride (for example 1500 to 2000 mg/d), glucosamine sulfate, glucosamine phosphate and N-acetyl glucosamine; glycosaminoglycanes (GAG) such as chondroitin sulfate (for example 800 to 1200 mg/d); glycosaminoglycane analogues such as polysulfated glycosaminoglycanes, or glycosaminoglycane precursors such as hyaluronic acid, glucuronic acid, iduronic acid, keratan sulfate, heparan sulfate, or dermatin sulfate; pentosan or its derivatives, in particular pentosan sulfate, pentosan polysulfate (PPS) and pentosan polysulfate polysaccharides; S-adenosylmethionine (SAMe); adenosine; superoxide dismutase (SOD); L-ergothionine; hydrolyzed or non hydrolyzed type II collagens; collagen hydrolysates such as gelatin; diacerin; arachadonic acid; tetracycline; tetracycline analogues; doxycycline; hydroxyproline; and mixtures thereof.

Advantageously, the compositions of the present invention include, in combination, a plurality of the compounds mentioned above. Particularly preferred compounds are glucosamine and chondroitin sulfate, alone or in combination.

In a particular implementation of the present invention, the compositions further comprise at least one compound selected from extracts of celery, green mussel, sea cucumber, or ovine, bovine, caprine, or marine (shark) cartilage, extracts from conventional keratin or keratec (cynatine FLX), adenosinemethionine sulfate, hyaluronic acid of all molecular weights, vitamins A (5000 IU), vitamins C (up to 1 g), vitamins E (100 IU to 400 IU), selenium (55 mcg (micrograms) to 200 mcg), flavonoids and alimentary compounds containing them such as: rutin, phellodendron amurensi extract, curcumin, garlic, lutein, zeaxanthin, lycopene, hesperidine, gingko, OPC (all up to 1 g/d), EPA from algae, plankton, krill, or fish (up to 2 g/d), DHA, LA (linoleic acid), or ALA.

The compositions of the present invention may also include compounds such as growth hormone (somatotrophin), somatomedins, insulinoid growth factors, as well as analgesics of the acetaminophene or tramadol type, or non-steroidal anti-inflammatories or anti-COX2.

The compositions of the present invention may also include oligo-elements such as boron, copper, magnesium, manganese, selenium (for example 55 to 200 mg), silica, zinc, and derivatives thereof.

The compositions of the present invention may also include vitamins (A, C, D, E, K, B3, B5, B6, B12).

The compositions of the present invention may also include compounds capable of limiting bone degradation and/or encouraging bone remineralization, such as biphosphonates, calcium, beta-blockers, phytoestrogens, raloxifen, or strontium.

The compositions of the present invention may also include plant extracts, in particular bromealin, harpagophytum, ginger, gingko biloba, centellia asiatica, kava-kava, valerian, wild yam, or celery.

The compositions may also include antioxidants such as glutathione, N-acetyl cysteine, MSM (methylsulfonide methane), extracts of tea, in particular green tea, sulforaphane from broccoli, or aqueous pomegranate extracts.

The compositions of the present invention may also include hormones, such as melatonin or DHEA.

Advantageously, the compositions of the present invention also comprise matrix metalloprotease inhibitors (MMPs) such as lupin peptides.

The term "matrix metalloprotease inhibitors (MMPs)" as used in the present invention means any compound which is known to the skilled person for its ability to inhibit degradation of the extracellular matrix by MMPs. MMPs constitute a family of enzymes (currently more than twenty have been identified and characterized), zinc-dependent, with a highly conserved structure, which have the ability to degrade the components of the extracellular matrix. They are classified into collagenases, gelatinases, and stromelysin according to the nature of their substrate. The MMPs group thus is constituted by four sub-classes: (1) collagenases, (2) gelatinases, (3) stromelysins, and (4) membrane type MMPs (MT-MMPs). The activity of MMPs may be modulated by naturally present proteinase inhibitors such as tissue inhibitors of metalloproteinase (TIMPs; in particular TIMP-1 and TIMP-2). In particular, an active compound is used to inhibit at least one MMP selected from the group constituted by MMP-1, MMP-2, MMP-3, MMP-9, MMP-7, MMP-13 and MMP-18. The term "MMP inhibitor compound" in particular means tissue inhibitors of metalloproteinase (TIMPs), alpha-2-macroglobulin, plasminogen activator inhibitors, zinc chelators, bryostatin-1, antibiotics (doxycyclins, minocyclins, etc), synthetic or natural peptides with a structure similar to the MMP substrates (batimastat, marimastat, etc), retinoids (in particular non aromatic retinoids such as retinaldehyde, tretinoin, 9-cis retinoic acid, vitamin A, monoaromatic retinoids such as etretinate, all-trans acitretine and motrerinide, and polyaromatic retinoids such as adapalene, tazarotene, tamibarotene and sulfone methyl arotinoid), antioxidants (oxygen radical scavengers, etc), anti-cancer agents (or anti-metastatics), malt hydrolysates such as Colalift sold by Coletica, marine algae extracts such as Kelpadélie sold by Secma, shark cartilage extracts such as MDI complex sold by Atrium, rice peptides such as Colhibin sold by Pentapharm, for example, and lupin peptide extracts. More particularly, the MMP inhibitor compound of the present invention is selected from the group constituted by lupin peptide extracts or "lupin peptides" such as those described in French patent application FR-A-99/04 875 filed on 19th Apr. 1999 in the name of Laboratoires Expanscience. In particular, the peptide extract described in FR-A-99/04 875 and designated extract B (LU105) may be mentioned. In a further preferred implementation of the invention, the compositions of the invention contain the MMP inhibitor selected from the group constituted by retinoids.

The present invention also pertains to said compositions or the refined avocado oil of the invention for use as a medication, a dermatological agent, as a cosmetic agent or as a nutriceutical, for human or animal use. Said compositions or refined avocado oil of the invention are advantageously used in veterinary applications.

The refined avocado oil and compositions of the present invention may be administered to an animal or human being, advantageously by a topical or oral route.

The compositions of the present invention may in particular be in any appropriate dosage form, in particular in the form of an aqueous or hydroalcoholic lotion, monophase or polyphase, a monophase or polyphase gel, an emulsion, a cream, a vesicular dispersion, a foam, or a spray.

Particularly advantageously, the refined avocado oil or compositions of the present invention may also be used in the prevention or treatment of cardiovascular disease, articular diseases such as arthritis, rheumatism, periodontal diseases such as gingivitis or periodontitis, inflammations, or in the prevention or treatment of the degradation of the extracellular matrix, in the prevention or treatment of skin ageing, or for gum, cartilage, and skin health.

Because of its fatty acid profile, the refined avocado oil of the present invention is very close to that of olive oil. Because of its aroma, heat resistance and nutritional qualities, avocado oil may be used for cold culinary use (salads, vinaigrettes, mayonnaises, etc) or hot culinary use (cooking oil, frying oil, etc).

The use in combination with flavorings or vegetable extracts can bring out the nutritional qualities of said oil and its originality as regards culinary preparations.

The refined avocado oil of the present invention has a high monounsaturated fatty acid content. It is now recognized that a diet rich in monounsaturated fatty acids reduces the overall cholesterol level and that of bad cholesterol (LDL) and increases that of good cholesterol (HDL). Since the 1950s, more than 600 scientific studies have shown that a diet rich in phytosterols helps to control total cholesterol and LDL cholesterol levels in the blood of animals and people.

Because of the composition of its sterol-rich unsaponifiables fraction, the refined avocado oil of the present invention can participate to advantage in controlling cholesterol levels in the blood. Hence, these properties render refined avocado oil particularly favorable for use as a food oil or as a food complement. The refined avocado oil of the present invention is also advantageously used to treat excess weight or to prevent weight gain.

To this end, the compositions of the present invention may contain, in combination with the refined avocado oil, hypolipemic molecules such as fibrates (fenofibrate: PPAR-alpha agonist), HMG-CoA reductase inhibitors (lovastatin, simvastatin). Hypoglycemating plants which may also be used in the context of the present invention in combination with the refined avocado oil are advantageously selected from the group constituted by fenugreek (*Trigonella graenum*), corosolic acid (active compound in leaves from the tree *Lagestroemia speciosa*), *Gymnema sylvestre*, balsam apple fruit juice (*Momordica charantia*), eucalyptus (*Eucalyptus globulus*), *Panax ginseng*, or bilberry leaves (*Vaccinum myrtillus*).

The refined avocado oil or the compositions of the present invention may also be used as medication for a variety of therapeutic applications. The refined avocado oil advantageously plays an essential role in the prevention or treatment of cardiovascular diseases or in the control of blood cholesterol levels. The refined avocado oil of the invention may also be used to treat obesity or diabetes.

In the context of cardiovascular disease, the refined avocado oil may be used in combination with anti-diabetic treatments such as oral diabetes treatments. Insulin therapy for type 2 diabetes may be mentioned and/or various treatments such as glucose captors and an artificial pancreas. An example of an oral diabetes treatment which may be mentioned is the stimulation of insulin secretion (hypoglycemiating sulfamide or the like (tolbutamide, carbutamide, glicazide, glimepiride, glipizide), a metformin derivative (benfluorex), alpha-glucosidase inhibition (acarbosis and miglitol), the treatment of insulin resistance (thiazolidinediones (or glitazone), such as rosiglitazone and pioglitazone), or treatments for obesity such as serotonin reuptake inhibitors (sibutramin), lipid digestion inhibitors (orlistat), agonists for the adrenergic beta 3 receptor (augmentation of lipolysis and thermogenesis), augmentation of the peripheral use of glucose by reducing fatty acid oxidation), or insulin secretion with GP1, pramlintide, IGF1 and vanadium derivatives, or glinides.

In the context of the prevention of cardiovascular diseases, the refined avocado oil may be used in combination with anti-obesity treatments. The anti-obesity treatments which may be used in the context of the present invention in combination with the refined avocado oil are advantageously selected from the group constituted by orlistat (Xenical®) and sibutramin (Reductyl® or Sibutral®).

Anti-fat nutrients which may be used in the context of the present invention in combination with the refined avocado oil, advantageously with a synergistic effect, are advantageously selected from the group constituted by nutrients which block fat absorption, such as chitosan, which is a fiber extracted from crustacean exoskeletons, nutrients which are capable of augmenting thermogenesis ("fat burners") such as ephedrin (the Chinese herb Ma Huang), caffeine, theine and the citrus aurantium, CLA (conjugated linoleic acid, preferably from safflower), omega 3-rich fish oils, cactus palm lipid captors, dry extracts of nutrients capable of regulating the appetite ("hunger busters") such as L-phenylalanine and L-tyrosine, nutrients capable of regulating glycemia, such as minerals, for example chromium or vanadium or magnesium, or the ayurvedic herb *Gymnema sylvestre*, lipogenesis inhibitors, such as hydroxycitric acid extracted from *Garcinia cambodgia* and nutrients capable of transporting fat, such as L-carnitine.

The refined avocado oil or compositions of the present invention may also be used as medication intended for tissue repair, or for the treatment of skin inflammation or irritation of the skin, body hair or mucosae, in particular for the treatment of eczema, psoriasis, pruritis, ichthyosis, acne, xerosis, atopical dermatitis, atopic skin, or allergic skin.

The refined avocado oil or compositions of the present invention may also be used as a medication in rheumatological or dental applications, possibly in combination with a treatment via bone substitutes.

The term "bone substitutes" means, for example, calcium phosphate ceramics, injectable ionic cements, composite materials, bone substitutes of animal origin, or derived from coral. Said compounds are advantageously used in the following applications: reconstruction of loss of bony substance after a complete hip replacement, augmentation of alveolar crest, periodontal fillings, compressive cervical foraminotomy, posterior cervical and vertebral arthrodesis, mastoid filling, repair to the anterior base of the cranium, filling zones from which iliac bone grafts have been taken, correcting facial bone contours, filling traumatic bone cavities and fractures of the long bones of the lower members.

In particular, the refined avocado oil or compositions of the present invention may also be used to treat and/or prevent joint diseases, such as arthritis, or periodontal diseases such as gingivitis or periodontitis.

In the context of dental applications, the refined avocado oil may be associated with antibiotics, anti-plaque agents, MMP inhibitors or anti-inflammatories.

The refined avocado oil of the invention may advantageously be used in combination with peptide extracts of avocado and/or avocado sugars, or with cutaneous and buccal antibacterials such as cathelicidins and defensins, in particular human cathelicidin, α-defensins, β-defensins, in particular hBD-1, hBD-2, hBD-3, and hBD-4, or other peptides and proteins such as adrenomedullin, cystatin or the elastase-specific inhibitor, more particularly elafin (SKALP).

The avocado peptide extract which may be used in combination with the refined avocado oil of the invention typically contains 2% to 10% by weight of alpha-amino nitrogen relative to the dry matter weight of the peptide extract.

The avocado peptide extract may be obtained by a process comprising the following steps:
  producing an avocado press cake, advantageously from avocado fruit, by drying then extracting with oil; then
  cryogrinding and complete delipidization of said press cake followed by decanting, centrifuging, and cake recovery; then
  a first hydrolysis in the presence of glucanases, followed by centrifuging and eliminating the soluble fraction;
  a second hydrolysis in the presence of one or more proteases, followed by centrifuging and eliminating the residue; then
  concentrating the peptide phase by nanofiltration and, if necessary, decolorization in the presence of activated charcoal; then
  simple filtration (10 μm (micrometers)) followed by ultrafiltration (cutoff threshold 10 kD (kilodaltons)); finally
  if appropriate, adding preservative, final sterilizing microfiltration (0.2 μm) and packaging.

Advantageously, the avocado peptide extract has the following amino acid content, as a percentage by weight relative to the total weight of amino acids:

| | |
|---|---|
| Alanine | 6.4-7.8 |
| Arginine | 4.7-5.7 |
| Aspartic acid | 10.3-12.7 |
| Cystine-cysteine | 2.9-3.5 |
| Glutamic acid | 13.0-15.8 |
| Glycine | 5.3-6.5 |
| Histidine | 2.2-2.6 |
| Isoleucine | 4.8-5.8 |
| Leucine | 7.6-9.4 |
| Lysine | 3.0-3.8 |
| Methionine | 1.2-1.6 |
| Phenylalanine | 4.7-5.7 |
| Proline | 4.1-5.2 |
| Serine | 5.5-6.7 |
| Threonine | 4.6-5.6 |
| Tyrosine | 3.6-4.4 |
| Valine | 5.8-7.2 |

Typically, the compositions of the invention contain the refined avocado oil as well as 0.1% to 20% dry weight of avocado peptide extract relative to the total composition weight.

The avocado sugars extract which may be used in combination with the refined avocado oil of the invention is typically a hydrosoluble extract of avocado sugars and advantageously contains D-mannoheptulose and/or perseitol.

In an advantageous variation of the invention, the composition comprises the refined avocado oil of the invention in combination with D-mannoheptulose and/or perseitol (C7 sugars) or a chemical derivative thereof. The composition advantageously has a 0.1% to 30% dry weight avocado sugar content relative to the total composition weight.

The hydrosoluble avocado sugars extract is obtainable by a process comprising the following steps in succession:
  obtaining an avocado press cake, advantageously from the fruit of the avocado, by drying avocado then extracting lipids (oil); then
  cryogrinding and complete delipidation of said press cake then decanting and centrifuging to recover a soluble fraction which is rich in C7 sugars (elimination of cake);
  demineralizing said soluble fraction obtained in the preceding step on ionic resin; then
  ultrafiltration at 10000 daltons;
  if appropriate, concentration by vacuum evaporation, adding preservative, sterilization by microfiltration (0.2 μm), and packaging.

The refined avocado oil or compositions of the present invention may also be used in cosmetic compositions intended to treat, repair, or protect the skin or dry mucosae, as well as dry or dull hair. The oil or compositions of the present invention may also be used for the cosmetic treatment of problems linked to ageing of the skin, the near mucosae and/or hair or nails, for the treatment of skin problems, the close mucosae and/or hair or nails resulting from exposure to actinic radiation, in particular UV radiation, for the treatment of problems of the skin, the near mucosae and/or hair or nails resulting from exogenic stress (pollution etc) or endogenic stress, or as softening agents, regenerating agents, or strengthening agents for the hair.

The compositions of the present invention may, for example, contain cosmetically or pharmaceutically acceptable excipients as well as conventional cosmetic additives, in particular organic or mineral UVB/UVA filters, antioxidants, free radical scavengers, irradiated cell protectors, natural or synthetic substances capable of stimulating the synthesis of cutaneous lipids, or anti-ageing agents which are known to the skilled person (retinoids, vitamins, etc).

The following examples are given by way of non limiting illustration of the present invention. All the percentages indicated are percentages by weight.

EXAMPLE 1

Starting material: This was constituted by fresh avocados of the Fuerté variety, of South African origin. The average amount of oil in the fresh avocados was 16% by weight.

Drying the fruit: 20 kilograms (kg) of whole fresh avocado was sliced into 2 millimeters (mm) to 50 mm slices using a disk knife and distributed onto trays at a thickness of 4 centimeters (cm) to 5 cm. Drying was carried out in a heat-regulated oven at a temperature of 70° C. for 48 h. The dried fruit was then ground in a roller grinder. The weight of dried fruit recovered was 5.56 kg, i.e. 27.8% of the starting material.

Oil extraction: This operation was carried out in a Komet type laboratory press. The extracted oil was filtered through a Buchner flask then stored under nitrogen away from light and moisture. 1750 g of unrefined avocado oil was extracted, i.e. 31.5% of the dried fruit employed.

The unrefined oil obtained was separated into two portions to carry out two comparative refining tests.

a) Process Including a Molecular Distillation Step:

Fractioning/concentration: The concentration step was carried out using a Leybold KDL 4 type wiped film molecular distiller. The temperature was fixed at 230° C. and the vacuum at $10^{-3}$ mmHg. The yield of distillate from this operation was 10.4% and the heavy fraction represented 89.6% of the unrefined oil employed.

Heavy fraction refining: 200 g of the heavy fraction of the unrefined avocado oil was heated to 76° C. in a 500 ml conical reactor with stirring, then 0.05% of phosphoric acid was added. Contact was maintained for 45 minutes, with stirring. A sodium hydroxide solution was added, and stirring was maintained until soap formation was complete. The lower phase containing the soaps was then withdrawn after decanting. The upper organic phase was washed with water to neutral pH. After drying under vacuum at 90° C., 3% of Norit SA4 charcoal and 5% of decolorizing earth were added and contact was maintained for ½ hour with stirring. The mixture was then filtered. The decolorized avocado oil was steadily chilled with gentle stirring to a temperature of 12° C. The oil was maintained at this temperature for 48 h, and filtered under pressure. The decolorized and winterized avocado oil then underwent deodorization at 180° C. at 4 mbars (millibars). The vapor was injected into the oil at a rate of 0.4 l/min (liters/min) for 4 h. After drying and cooling, refined avocado oil was obtained.

Storage: The refined avocado oil (152 g) was then stored in an inert gas away from light and moisture.

Analysis:
Density: 0.914
Refractive index: 1.471
Acid value: 0.1 mg of KOH/g
Peroxide index: 0.2 meq/kg (milli-equivalents/kg)
Cold behavior: clear after 2 h at −5° C.
Gardner color: 2.9
Unsaponifiables content: 0.6%
Fatty Acid Composition:
palmitic acid: 16%
palmitoleic acid: 7.2%
oleic acid: 60%
linoleic acid: 15.2%
linolenic acid: 0.5%
arachidic acid: 0.3%
Persin: not detected
Avocado furanic lipids: not detected
Composition of Unsaponifiable Fraction:
Sterols content: 52.9 g/100 g of unsaponifiable fraction
Squalene content: 0.32 g/100 g of unsaponifiable fraction
Relative Sterol Composition:
Campesterol: 4.6%
Stigmasterol: 1.67%
Beta sitosterol: 48.96% b) Process not Including a Molecular Distillation Step

Refining unrefined avocado oil: 200 g of the unrefined avocado oil was heated to 76° C. in a 500 milliliters (mL) conical reactor with stirring, then 0.05% of phosphoric acid was added. Contact was maintained for 45 minutes, with stirring. A sodium hydroxide solution was added, and stirring was maintained until soap formation was complete. The lower phase containing the soaps was then withdrawn after decanting. The upper organic phase was washed with water to neutral pH. After drying under vacuum at 90° C., 3% of Norit SA4 charcoal and 5% of decolorizing earth were added and contact was maintained for ½ hour with stirring. The mixture was then filtered. The decolorized avocado oil was steadily chilled with gentle stirring to a temperature of 12° C. The oil was maintained at this temperature for 48 h, and filtered under pressure.

The decolorized and winterized avocado oil then underwent deodorization at 180° C. at 4 mbars. The vapor was injected into the oil at a rate of 0.4 L/min (liters/min) for 4 h. After drying and cooling, refined avocado oil was obtained.

Storage: The refined avocado oil (170 g) was then stored in an inert gas away from light and moisture.

Analysis:
Gardner color: 9.0
Unsaponifiables content: 4.42%
Fatty Acid Composition:
palmitic acid: 20.9%
palmitoleic acid: 8.8%
oleic acid: 58.4%
linoleic acid: 10.4%
linolenic acid: 0.6%
arachidic acid: 0.2%
Acetogenins: 400 ppm
Avocado furanic lipids: 2.25 g/100 g
Composition of Unsaponifiable Fraction:
Sterols content: 14.1 g/100 g of unsaponifiable fraction
Squalene content: 3.11 g/100 g of unsaponifiable fraction
Relative Sterol Composition:
Campesterol: 8.19%
Stigmasterol: 14.94%
Beta sitosterol: 40.42%

It can thus be seen that the process of the present invention, comprising a molecular distillation step in particular, can produce an oil which is substantially free of acetogenins and furanic lipids and which is much easier to decolorize.

EXAMPLE 2

Comparative analyses of the glyceride composition of oils obtained by the process of the invention with oils obtained by a prior art process including cold pressure extraction and chemical refining:

Tests 1 and 2 corresponded to two oils of the present invention, using the process described in Example 1, starting from two different starting materials.

Samples 1 and 2 are samples of commercially available prior art oils.

Comparative analyses of the glyceride composition are shown in Table 1 below:

TABLE 1

| Product | Triglycerides | Diglycerides | Monoglycerides |
|---------|---------------|--------------|----------------|
| Test 1  | 97.43%        | 2.57%        | ND             |
| Test 2  | 97.81%        | 2.19%        | ND             |
| Sample 1| 89.04%        | 3.51%        | 6.39%          |
| Sample 2| 89.04%        | 3.10%        | 5.20%          |

These comparative analyses demonstrate the impact of molecular distillation used to produce test oils 1 and 2 (as described in Example 1) on fractioning avocado oil glycerides. This process demonstrates the elimination of partial glycerides (mono- and di-glycerides) and enrichment in triglycerides.

The invention claimed is:

1. A composition containing compounds containing ω-3 derivatives and a refined avocado oil rich in triglycerides, the latter may be obtained by a process comprising the following steps:
   1) dehydrating fresh avocados or avocados which have undergone prior transformations, in controlled manner;
   2) extracting oil from the dehydrated fruit;
   3) fractioning the oil into its fraction rich in triglycerides; then
   4) refining the oil fraction rich in triglycerides.

2. The composition according to claim 1; wherein the refined avocado oil, which is rich in triglycerides, contains an unsaponifiable fraction which is rich in sterols.

3. The composition according to claim 2; wherein the unsaponifiable fraction of the refined avocado oil contains at least 40% by weight of sterols.

4. The composition according to claim 3; wherein the unsaponifiable fraction of the refined avocado oil contains between 45% and 70% by weight of sterols relative to the total weight of unsaponifiables.

5. The composition according to claim 1; wherein the refined avocado oil, which is rich in triglycerides, contains at most 100 ppm of acetogenins and at most 500 ppm of furanic lipids relative to the total weight of oil.

6. The composition according to claim 1; wherein the refined avocado oil may be obtained by a process in which the fractioning step 3) is selected from the group consisting of cold crystallization, vacuum distillation, or molecular distillation.

7. The composition according to claim 6; wherein the refined avocado oil may be obtained by a process in which the fractioning step 3) is molecular distillation which is carried out at a temperature in the range 180° C. to 260° C., maintaining the pressure in the range $10^{-3}$ mmHg to $10^{-2}$ mmHg.

8. The composition according to claim 6; wherein the refined avocado oil may be obtained by a process in which the fractioning step 3) is molecular distillation which is carried out in a device selected from the group consisting of centrifugal type molecular distillers and molecular distillers of the wiped film type.

9. The composition according to claim 1; wherein compounds containing ω-3 derivatives are selected from the group consisting of:
   vegetable oils rich in ω-3;
   animal oils rich in ω-3;
   algae;
   plankton;
   krill;
   shark cartilage;
   eicosapentanoic acid;
   docohexanoic acid;
   linolenic acid; and
   alpha-linolenic acid
   and their mixtures.

10. The composition according to claim 9; wherein the vegetable oil is linseed oil.

11. The composition according to claim 9; wherein the animal oil is fish oil.

12. The composition according to claim 11; wherein the fish oil is fish-liver oil.

13. The composition according to claim 9; wherein the compound containing ω-3 derivatives is algae extract or algae oil.

14. The composition according to claim 9; wherein the compound containing ω-3 derivatives is krill oil.

15. The composition according to claim 9; wherein the algae is microalgae or macroalgae.

16. The composition according to claim 1, containing the refined avocado oil rich in triglycerides at a concentration in the range 5% to 95% by weight relative to the total composition weight.

* * * * *